(12) United States Patent
Törmälä et al.

(10) Patent No.: US 6,350,284 B1
(45) Date of Patent: *Feb. 26, 2002

(54) BIOABSORBABLE, LAYERED COMPOSITE MATERIAL FOR GUIDED BONE TISSUE REGENERATION

(75) Inventors: Pertti Törmälä; Minna Kellomäki, both of Tampere; Timo Waris, Helsinki, all of (FI)

(73) Assignee: Bionx Implants, Oy, Tampere (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/152,437

(22) Filed: Sep. 14, 1998

(51) Int. Cl.$^7$ .................................................. A61F 2/44
(52) U.S. Cl. .................................. 623/17.19; 623/16.11
(58) Field of Search ............................ 606/70, 71, 72, 606/66, 67, 68; 623/11, 16, 18

(56) References Cited

U.S. PATENT DOCUMENTS

| | | | |
|---|---|---|---|
| 4,186,448 A | * 2/1980 | Brekke ........................ | 3/1.9 |
| 4,338,926 A | * 7/1982 | Kummer et al. .............. | 128/92 |
| 4,400,833 A | 8/1983 | Kurland | |
| 4,778,472 A | * 10/1988 | Homsy et al. ................ | 623/18 |
| 4,839,215 A | * 6/1989 | Starling et al. .............. | 428/131 |
| 4,898,186 A | 2/1990 | Ikada et al. | |
| 4,968,317 A | 11/1990 | Törmälä et al. | |
| 5,013,315 A | * 5/1991 | Barrows ....................... | 606/71 |
| 5,084,051 A | * 1/1992 | Tormala et al. ............... | 606/77 |
| 5,380,328 A | * 1/1995 | Morgan ........................ | 606/70 |
| 5,489,305 A | * 2/1996 | Morgan ........................ | 623/16 |
| 5,591,234 A | * 1/1997 | Kirsch ......................... | 623/16 |
| 5,728,157 A | * 3/1998 | Prescott ....................... | 623/11 |
| 5,916,585 A | * 6/1999 | Cook et al. .................. | 424/426 |
| 5,824,088 A | * 10/1999 | Kirsch ......................... | 623/16 |
| 5,980,540 A | * 11/1999 | Bruce .......................... | 606/15 |

FOREIGN PATENT DOCUMENTS

| | | |
|---|---|---|
| EP | 0274898 | 7/1988 |
| GB | 2085461 | 4/1982 |
| WO | WO 90/04982 | 5/1990 |
| WO | WO 90/12605 | 11/1990 |
| WO | WO 92 10218 | 6/1992 |
| WO | WO 92/10218 | * 7/1992 |
| WO | WO94/15588 | 7/1994 |
| WO | WO 95 28900 | 11/1995 |
| WO | WO 96/00592 | 1/1996 |
| WO | WO96/41596 | 12/1996 |
| WO | 96/41596 | * 12/1996 |
| WO | WO 98 07384 | 2/1998 |
| WO | WO98/14134 | 4/1998 |
| WO | WO 98/30252 | 7/1998 |

OTHER PUBLICATIONS

R.M. Pilliar, Powder Metal–Made Orthopedic Implants with Porous Surface for Fixation by Tissue Ingrowth, Clinical Orthopaedics and Related Research, vol. I 176, 1983, pp. 42–51.

S. Vainiopaa, et al, Surgical Applications of Biodegradable Polymers in Human Tissues, Progress in Polymer Science, vol. 14, 1989, pp. 679–716.

J. Eitenmüller, et al., An In Vivo Evaluation of a New High Molecular Wt. Polylactide Osteosynthesis Device, European Congress on Biomaterials, Bologna Italy, Sep. 14–17, 1986, p. 94.

(List continued on next page.)

Primary Examiner—Corrine McDermott
Assistant Examiner—Hieu Phan
(74) Attorney, Agent, or Firm—Kenyon & Kenyon

(57) ABSTRACT

This invention describes a rigid layered composite material including a bioabsorbable plate layer and a bioabsorbable web layer for guided bone tissue regeneration, particularly suited for use in the treatment of cranial bone defects.

14 Claims, 1 Drawing Sheet

OTHER PUBLICATIONS

Törmälä, Biodegradable Self–Reinforced Composite Materials; Manufacturing Structure & Mechanical Properties, Clinical Materials, vol. 10, 1992, pp. 29–34.

O.H. Andersson, et al., Bioactive Glass, Biomaterials Today and Tomorrow, Proceedings of the Finnish Dental Society Days of Research, Tampere, Finland, Nov. 10–11, 1995, pp. 15–16.

J.C. Behiri, et al., Advanced Bone Cement For Long Term Orthopaedic Applications, Bioceramics, vol. 4 Edited by W. Bonfield, et al., Processing of the 4th International Symposium on Ceramics in Medicine, London, UK, Sep. 1991, Butterworth—Heinemann Ltd., Oxford, 1991, pp. 301–307.

W. Bonfield, et al., In Vivo Evaluation of Hydroxyapatite Reinforced Polyethylene Composites, Biological & Biomechanical Performance of Biomaterials, Edited by P. Christel, et al., Elsevier Science Publishers, 1986, pp. 153–158.

C. Doyle, et al., In Vitro & In Vivo Evaluation of Polyhydroxybutyrate and of Polyhydroxybutyrate Reinforced with Hydroxyapatite, Biomaterials, vol. 12, 1991, pp. 841–847.

Chase S. W., Herndon C.H., "The fate of autogenous and homogenous bone grafts: A historical review," *Journal of Bone Joint Surgery* 37 A, 1955, pp. 809–841.

Prolo D.J., "Cranial defects and cranioplasty, in Wilkins RH, Rengachary SS (eds): Neurosurgery," New York, McGraw–Hill, 1984, pp. 1647–1656.

Grant F.C., Norcross N.C., "Repair of Cranial Defects By Cranioplasty," *Annual Surgery* vol. 110, 1939, pp. 488–512.

Reeves D.L., "Cranioplasty," Springfield, IL, Charles C. Thomas, 1950, pp. 3–119.

Woolf J.I., Walker A.E., "Cranioplasty, Collective review," *International Abstract Surgery* 81, 1945, pp. 1–23.

Habal M.B., Leake D.L., Maniscako J.E., "A new method for reconstruction of major defects in the cranial vault," *Surgery Neurology* 6, 1976, pp. 137–138.

Karvounis P.C., Chiu J., Sabin H., "The use of prefabricated polyethylene plate for cranioplasty," *Journal of Trauma* 10, 1970, pp. 249–254.

Black S.P.W., "Reconstruction of the supraorbital ridge using aluminum," *Surgery Neurology* 9, 1978, pp. 121–128.

Heller J., Poloy(ortho esters), Advances in Polymer Science 107: 41–92, 1993.

Peter D. Costantino, et al. "Synthetic biomaterials in Facial Plastic and reconstructive Surgery." *Facial Plastic Surgery* vol. 9, No. 1. Jan. 1993, pp. 1–15.

P. Törmälä et al., "Bioabsorbable polymers: materials technology and surgical applications," Proc. Instn. Mech. Engrs., vol. 212, Part H., pp. 101–111.

S. Paasimaa et al., Development of a Bioabsorbable Finger Joint Prosthesis: Material Selection, $13^{th}$ European Conf. On Biomaterials, Sep. 407, 1977, pp. 146.

Rogers et al., "Absorbable Mesh Splenorrhaphy for Severe Splenic Injuries: Functional Studies in an Animal Model and an Additional Patient Series," The Journal of Trauma, vol. 31, No. 2, 1991, pp. 200–204.

Nagy et al., "Experience with Three Prosthetic Materials in Temporary Abdominal Wall Closure," The American Surgeon, vol. 2, May, 1996, pp. 331–335.

Rahman, et al., "Silicone Granulomatous Reactions After First Metatarsophalangeal Hemiarthroplasty," British Editorial Society of Bone and Joint Surgery, Vo. 75–B, No. 4, Jul. 1993, pp. 637–639.

Kossovsky et al., "An Unusual Case of Biomaterials Pathology Discovered at Autopsy Using X–Ray Energy Spectroscopic Techniques," Biomaterials Bioreactiviy Characterization Laboratory and Division of Anatomic Pathology, Apr. 7, 1989, pp. 148–152.

Ashammakhi et al., "Strength retention of self–reinforced polyglycolide membrane: an experimental study," Biomaterials 1995, vol. 16, No. 2, pp. 135–138.

Pizzoferrato et al, "Biomaterials and Clinical Applications," Proceedings of the Sixth European Conference on Biomaterials, Bologna, Italy, Sep. 14–17, 1986; 759–764.

McDowell et al., "The McDowell Series of Plastic Surgical Indexes," vol. 1, The Zeis Index and History of Plastic Surgery 900 B.C.–1863 A.D., pp. 51–52.

* cited by examiner

BIOABSORBABLE, LAYERED COMPOSITE MATERIAL FOR GUIDED BONE TISSUE REGENERATION

BACKGROUND OF THE INVENTION

The present invention describes a bioabsorbable layered surgical implant comprising two components. One component is a solid plate of bioabsorbable polymer and the other is a web made of bioabsorbable fibers. These implants guide and enhance bone healing and protect the soft tissues beneath the healing bone. These implants are particularly useful in cranioplasty.

Guided bone regeneration by means of implants has a long history, especially in cranioplasty, where there exists a great need to prevent damage to the brain by covering holes and other defects in cranial bone. The materials used to effect guided bone regeneration, such as would occur in cranioplasty, must meet several criteria. They must have, for example, good biocompatibility and high mechanical strength. Further, they should not cause bone erosion.

In the past, bone tissue grafts have been made, for example, as allografts from canine bone, human bone, decalcified bone, pericranium, and as autografts from the tibia, rib and crista iliac. See Zeiss Index and History of Plastic Surgery 900 BC–1863 AD Baltimore, Williams & Wilkins, 1977, vol 1, pp 51–52; Chase S. W., Herndon C. H., The fate of autogenous and homogenous bone grafts: A historical review, Journal of Bone Joint Surgery 37 A, 1955, pp. 809–841; Prolo D. J., Cranial defects and cranioplasty, in Wilkins R H, Rengachary S S (eds): Neurosurgery, New York, McGraw-Hill, 1984, pp 1647–1656; Grant F. C., Norcross N. C., Repair of Cranial Defects By Cranioplasty, Annual Surgery vol. 110, 1939, pp. 488–512; Reeves D. L., Cranioplasty, Springfield Ill., Charles C. Thomas, 1950; and Woolf J. I., Walker A. E., Cranioplasty, Collective review, International Abstracts Surgery 81, 1945, pp. 1–23, the entire disclosures of each of which are incorporated herein by way of this reference. However, there are problems associated with the use of bone tissue grafts. If the patient's own bone is used as a graft, a surgeon must perform an additional, traumatic operation to take the bone sample. If the bone graft is taken from another person or animal bone is used, viral contaminations or immunological problems are possible, even if the graft is treated to make it compatible with the patient's tissue.

Additionally, man-made biostable materials have been studied in cranioplasty applications, such as cellulose fibers, aluminum, gold, titanium, stainless steel, poly methyl methacrylate (PMMA), polyethylene and silicone. See Habal M. B., Leake D. L., Maniscako J. E., A new method for reconstruction of major defects in the cranial vault, Surgery Neurology 6, 1976, pp. 137–138; Karvounis P. C., Chiu J., Sabin H., The use of prefabricated polyethylene plate for cranioplasty, Journal of Trauma 10, 1970, pp. 249–254; and Black S. P. W., Reconstruction of the supraorbital ridge using aluminum, Surgery Neurology 9, 1978, pp. 121–128, the entire disclosures of each of which are incorporated herein by way of this reference. However, the clinical use of most of these materials has been rejected due to severe tissue reactions. Further, biostable implants are particularly ill-suited for cranioplasty in children because a biostable implant prevents the immature skull bone from growing to adult size and, therefore, the implant needs to be removed in a second surgical procedure.

Many of the problems of biostable materials can be solved with implants made of bioabsorbable polymers, which cause fewer inflammatory reactions. The bioabsorbable implants are also suitable for children, because these implants resorb totally and the degradation products disappear from the body via metabolic routes. Moreover, these materials can be chosen to degrade quickly enough so that the growth of the child's cranium is not restricted, thereby obviating the need for a second operation. Even with bioabsorbable plates, however, there is a desire to effect quicker bone regeneration and healing.

BRIEF SUMMARY OF THE INVENTION

Thus, it is a goal of the present invention to provide an implant, particularly for cranioplasty, that is bioabsorbable, yet strong enough to protect soft tissue, such as the brain, during the healing period.

It is further a goal of the present invention to provide an implant, particularly for cranioplasty, that may be easily shaped or formed and applied over a defect in a bone, such as the cranium.

It is further a goal of the present invention to provide an implant, particularly for cranioplasty, that will promote quick bone regeneration, thereby shortening the healing period.

It is further a goal of the present invention to provide an implant, particularly for cranioplasty, that will degrade quickly enough so as not to restrict the natural growth in children of the bone under repair.

These and other goals are met with the present invention, comprising a rigid and tough, yet easily shaped, layered bioabsorbable implant for guided bone tissue regeneration, which may be used as a bioabsorbable surgical cranioplasty implant. The implant described in more detail in this application comprises two components. One component is a solid plate of a bioabsorbable polymer and the other is a web, typically made of bioabsorbable fibers. These implants have a surface structure that promotes bone growth on one side and prevents tissue irritation on the other. Thus, implants of the present invention enhance bone healing and protect the soft tissues beneath the healing bone and around the implant.

BRIEF DESCRIPTION OF THE DRAWINGS

The present invention will be more fully described in conjunction with the accompanying diagram wherein.

DETAILED DESCRIPTION OF THE INVENTION

Figure 1:
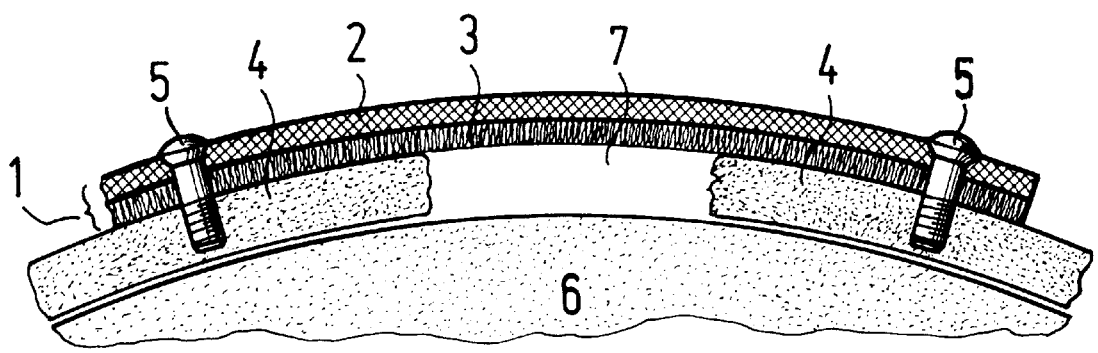
FIG. 1 is a cross-sectional schematic view of one embodiment of the implant of the present invention covering a cranial defect.

This invention relates to a bioabsorbable bone growth guiding implant, such as a cranioplasty implant, that adheres to bone, enhances growth and healing of the bone, and protects soft tissues, such as the brain, beneath the implant. The implant is manufactured by totally or partially joining together: (a) a solid and stiff bioabsorbable plate; and (b) a flexible and porous bioabsorbable web. These components are referred to herein as the (a) plate and (b) web layers. Both layers can be made of a bioabsorbable homopolymer, bioabsorbable copolymer, bioabsorbable polymer blend or polymer-based composite. These layers can be made of either the same or different materials, depending upon the particular application at hand. Possible biodegradable polymers to be used for the implant of the present invention are listed, e.g., in WO 96/41596, the entire disclosure of which is incorporated herein by way of this reference.

With reference to FIG. 1, which demonstrates an embodiment of the present invention, the implant can be implanted over the defect 7 in a bone 4, such as the cranium, to protect the tissues 6 inside or below the defect 7, such as those inside the skull, from being damaged. The implant 1 comprises two layers, the rigid plate layer 2 and the web layer 3.

The plate layer 2 determines the shape and size of the implant and has enough strength and stiffness to act as a protective shield for the tissue 6. It may be specially cut and shaped to easily and closely cover the defect 7 and the surrounding bone 4. In a preferred embodiment of the present invention, the top side of the plate layer 2 is smooth to avoid the irritation of surrounding tissues which could cause an adverse reaction in the patient.

The plate layer 2 may be made from any of the prior art biodegradable materials using techniques known in plastics technology, including extrusion, injection molding and/or solid state deformation, or pressing to the desired shape with or without heat. It is also possible to mechanically machine the plate layer to the desired shape. It is also possible to use a combination of techniques, for example, using machining to form a curved implant from an extruded sheet.

The thickness of the plate layer 2 will generally range from about 0.05 mm to about 3 mm, preferably from about 0.2 mm to about 1.5 mm. It is preferable to make the plate layer 2 as thin as possible, while still retaining enough rigidity to adequately protect the soft tissue 6. The thickness and other dimensions of the plate layer 2 (and implant 1) will depend on the size of the defect 7 to be covered, as well as the curvature of the surrounding bone 4 and, therefore, can vary greatly.

The web layer 3 is located below the plate layer 2 and above the bone 4 and the defect 7. It has been found, surprisingly, that the web layer 3 directs and enhances bone growth by providing a porous surface along which and into which the bone tissue can grow and spread. The web layer 3 is therefore located on the side of the implant that is placed against the bone 4 and the defect 7, The sizes of the pores in the web structure are controlled so as to favor bone growth.

The favorable pore size for promoting bone growth along the fibrous web layer 3 of the present invention has been discovered to be between about 30 $\mu$m and about 1000 $\mu$m. Typically, bone cells are not able to easily grow into pores smaller than about 30 $\mu$m. With pore sizes larger than about 1000 $\mu$m, bone growth is slower because there is less physical structure to which the bone cells can adhere themselves during regeneration. Most preferably, the pore size is between about 50 $\mu$m and about 400 $\mu$m, which best promotes bone growth.

In order to maintain the porosity of the web layer during the manufacturing of the implant 1, in a preferred embodiment of the present invention, the plate layer 2 and the web layer 3 are only partially or loosely attached to each other. This leaves a high degree of porosity in the surface structure of the web layer 3, which promotes rapid bone regeneration. The upper surface of the web layer 3 should be in contact with the plate layer 2, but not totally merged with the surface of the plate layer 2, thus leaving the web layer 3 porous.

The porous structure of the web layer can be manufactured from biodegradable fibers using any known methods from mechanical textile and plastics technology. The thickness of the fibers can vary from about 1 $\mu$m to about 200 $\mu$m. In a preferred embodiment of the invention, the fiber thickness is between about 5 $\mu$m and about 150 $\mu$m.

Structures suitable for the web component of this implant can be, for example, a cloth, a narrow fabric, a knit, a weave, a braid, or a web. In any case, the structure should be porous with pore size from about 30 $\mu$m to about 1000 $\mu$m, preferably between about 50 $\mu$m to about 400 $\mu$m. The web component can be manufactured using one type of fiber, for example polyglycolide or polylactide fibers. It is also possible to make the web using two or more different types of fibers depending upon the particular application and desired physical characteristics of the implant.

In a preferred embodiment of the present invention, the web layer 3 is made of biodegradable polymer that degrades faster than the polymer used for the plate layer 2. Thus, the web layer 3 degrades before the plate layer 2, allowing the bone to develop a more dense structure and attach to the surface of the plate before the plate disintegrates. The plate component remains and gives the desired strength, shape, and protection to the defect, while the regenerating bone increases its strength and density. Simultaneously, but as a slower process, bone may also cover the other side of the implant by growing on top of it, starting from the edges of the plate. Regardless, the implant finally resorbs, having been replaced with new bone and/or connective tissue. Resorption products disappear from the body via metabolic routes. In the end, the bone defect is covered or filled in by the patient's own regenerated bone.

The implant 1 can be fixed to the bone 4 with various attachment techniques known in the art, such as bioabsorbable sutures, bioabsorbable tacks, minitacks or microtacks, or bioabsorbable screws, depending on the implantation site and size of the implant. In FIG. 1, the implant 1 is attached to the bone 4 with small bioabsorbable screws 5.

The layers of the implant 1 may be joined to each other, e.g., by welding, as is described in a patent application to Paasimaa S., Kellomäki M., and Törmälä P., entitled "A bioabsorbable 2-dimensional multi-layer composite device and its manufacturing method," which is being filed concurrently herewith, or they can be glued, hot-pressed, ultrasonically welded or welded with some other technique. The layers of the implant 1 may remain separated before implantation, and joined during surgery by stitching them simultaneously to cover the cranial defect. They can also be joined together by attaching them to the bone using biodegradable tacks, minitacks, microtacks or miniscrews. These methods can also be used to attach the implant 1 with other prejoined components.

The implant 1 may contain various additives and modifiers that improve the processability of polymer, such as plasticizers and antioxidants. The components of the implant can also contain one or more bioactive, bone growth stimulating, or pharmaceutically active agents, like antibiotics, growth hormones or anticoagulants. Also, any bioceramic or bioactive glass (e.g., in the form of powder, flakes or fibers), which has been found to enhance bone healing, can be used as an additive. Typical examples of such bioceramics and bioactive glasses useful in this invention: hydroxyapatite, tricalcium phosphate and other calcium phosphates, Bioglass® (available from Research Center, University of Florida, Gainsville, Fla., USA), Ceravital®, Alumina, Zirconia, Bioactive gel-glass and other bioactive glasses.

According to a particularly advantageous embodiment of the present invention, the web layer is embedded with gel or paste containing bone growth factor(s), like NOVOS (made by and available from Stryker Biotech, Natic, Mass., USA), which comprises osteoconductive type I bone collagen and osteogenic protein 1. These growth factors induce and further stimulate the bone growth under the cranioplasty, thereby intensifying bone formation and healing.

After the description above of the present invention and certain specific embodiments thereof, it will be readily apparent to those skilled in the art that many variations and modifications may be made to the present invention without departing from the spirit and scope thereof. The following non-limiting examples further demonstrate various embodiments of the present invention.

EXAMPLE 1.

The repair of a 10×10 mm defect in the skull of adult New Zealand rabbits was carried out using each of the following five methods (A. through E.) to compare the rate of bone regeneration for each of those methods.

A. The soft tissues were closed over the defect.

B. A polylactide sheet of thickness 0.4 mm was prepared by extrusion of poly-D,L-lactide (D/L ratio 96/4), and a piece of size 15×15 mm was cut out from it, the corners rounded off and the plate bent to the desired convex form. The plate was fixed over the defect with DEXON stitches (available from Davis & Geck, USA) extending into the surrounding periosteum and the soft tissues were closed over it.

C. A piece of 0.15 mm thick polyglycolide membrane having a fibrous surface (Biofix®, available from and manufactured by Bionx Implants Ltd., Tampere, Finland) was cut to the shape of the plate described in method B, above, and placed over the defect with its fiber side towards the bone and defect. The plate described in method B, above, was placed on top of the defect and the membrane. The membrane and the plate were fixed in position with DEXON stitches extending into the surrounding periosteum and the soft tissues closed over them.

D. A piece of fiber web composed of polyglycolide fibers and bioactive glass fibers (composition of $Na_2O$, 6 mol. %; $K_2O$, 7.9 mol. %; MgO, 7.7 mol. %; CaO, 22.1 mol. %; $P_2O_5$, 1.7 mol. %; and $SiO_2$, 54.6 mol. %) was cut to the shape of the plate as described in method C above, and placed over the defect with a plate (as described in method B, above) on top of it. The plate and the web were fixed in position with DEXON stitches extending into the surrounding periosteum and the soft tissues were closed over the plate.

E. 50 μg recombinant growth factor (rTGF-β1, recombinant transgenic growth factor, available from and delivered by Helsinki University, Dept. Of Orthopedics and Traumatology) was mechanically mixed into a sterile 85/15 (wt. %/wt. %) blend consisting, respectively, of oligo L-lactate and copolymer of ∈-caprolactone and D,L-lactide (60/40 in D/L). The paste was painted onto the fibrous surface of a membrane as described in method C, above, and the membrane was then placed in position with the surface containing growth factor and polymer blend carrier towards the bone (and the defect). A plate of the kind described in method B, above, was placed on top of it, the membrane and the plate were fixed in position with DEXON stitches extending into the surrounding periosteum, and the tissues were closed over the plate.

Each procedure was performed in triplicate, and the animals were sacrificed after 12 weeks in all cases.

There occurred no bone growth in series A. In the case of series B, bone growth had proceeded to 40 percent of the defect area, but the defect was still partly filled with connective tissue in the center. Series C, D and E, which used implants according to the present invention, however, showed complete coverage of the defect by bone, although this was about 50 percent thinner in the center than at the edges in series C and 40 percent thinner in that respect in series D. In the series E, the new bone was only 30 percent thinner in the center of the defect than at the edges. Thus, with the implants of the present invention, it is possible to greatly increase the rate of cranial bone regeneration previously achieved with prior art biodegradable implants.

EXAMPLE 2.

The repair of a 10×10 mm defect in the skull of adult New Zealand rabbits was carried out using the following 2 methods, to compare the rate of bone regeneration for those methods.

A. A stiff plate was prepared by extrusion of poly(ortho ester) (a rigid copolymer of diketene acetal and 60:40 molar ratio of rigid and flexible diols manufactured as described in: Heller J., Poly(ortho esters), Advances in Polymer Science 107: 41–92, 1993, the entire disclosure of which is incorporated herein by way of this reference) to a thickness of 0.5 mm, and cut into pieces of size 15×15 mm. The corners of the plate were rounded off and the pieces bent to the desired convex form under heat. As shown in FIG. 1, the plate was fixed to the bone surrounding the defect using poly(ortho ester) mini-studs and the soft tissues were closed over the plate.

B. The inner surface of the plate described above in method A was moistened with a solvent, which made the surface of the plate tacky, and broken poly(ortho ester) fibers were sprinkled onto it so that they adhered to it and made the surface uneven and porous.

Each series (A and B) comprised 12 animals, of which 4 were sacrificed after 3 weeks, 4 after 24 weeks and 4 after 48 weeks. No soft tissue inflammatory reactions were seen in either series at the end of the experiment. No new bone tissue was observed in series A after three weeks, but 10 percent of the area of the defect had been covered by new bone in series B. After 24 weeks a coverage of 90 percent had been achieved in series A and full coverage in series B, while after 48 weeks the underside of the implant had become fully ossified in both series and some bone had been formed on the upper surface. As shown in FIG. 1, the plate was fixed to the bone surrounding the defect using poly (ortho ester) (the same copolymer as described above in method A) mini-studs.

We claim:

1. A bioabsorbable cranial implant comprising: a bioabsorbable rigid plate layer having upper and lower sides, and a bioabsorbable fibrous web layer in at least partial contact with the lower side of the rigid plate layer, said fibrous web layer having a porous surface along which and into which bone tissue can grow, wherein the fibrous web layer contains pores that are between 30 μm and 1000 μm in diameter and wherein the cranial implant is capable of being completely resorbed.

2. The implant of claim 1 wherein the rigid plate layer comprises bioabsorbable homopolymer, copolymer, polymer blend, or polymer composite.

3. The implant of claim 1 wherein the fibrous web layer comprises bioabsorbable homopolymer, copolymer, polymer blend, or polymer composite.

4. The implant of claim 1 wherein the rigid plate layer and the fibrous web layer are made of the same material.

5. The implant of claim 1, wherein the pores are between 50 μm and 400 μm in diameter.

6. The implant of claim 1 wherein the implant further comprises bioceramic glass.

7. The implant of claim 1 wherein the implant further comprises a bioactive agent.

8. A method for performing cranioplasty comprising the step of:

at least partially attaching the implant of claim 1 to a defect in a cranium so that the fibrous web layer abuts the cranium.

9. The implant of claim 1 wherein the rigid plate layer and the web layer are loosely attached to each other.

10. The implant of claim 1 wherein the rigid plate layer and the web layer are joined together by welding.

11. The implant of claim 1 wherein the rigid plate layer and the web layer are joined together by gluing.

12. The implant of claim 1 wherein the rigid plate layer and the web layer are joined together by hot-pressing.

13. The implant of claim 1 wherein the fibrous web layer bioabsorbs faster than the rigid plate layer.

14. An at least partially bioabsorbable cranial implant comprising:

a bioabsorbable rigid plate layer having upper and lower sides, a bioabsorbable fibrous web layer in at least partial contact with the lower side of the rigid plate layer, said fibrous web layer containing pores that are between 30 $\mu$m and 1000 $\mu$m in diameter, wherein the material of the fibrous web layer bioabsorbs faster than the material of the rigid plate layer, and the cranial implant is capable of being completely resorbed.

\* \* \* \* \*

UNITED STATES PATENT AND TRADEMARK OFFICE
CERTIFICATE OF CORRECTION

PATENT NO. : 6,350,284 B1
DATED : February 26, 2002
INVENTOR(S) : Gregory Pinchasik It is certified that error appears in the above-identified patent and that said Letters Patent is hereby corrected as shown below:

<u>Column 1,</u>
Line 31, "Abstract" should be -- abstracts --

<u>Column 6,</u>
Line 23, "comers" should be -- corners --

Signed and Sealed this

Third day of September, 2002

Attest:

JAMES E. ROGAN
Attesting Officer    Director of the United States Patent and Trademark Office